US012797001B2

(12) United States Patent
Lei et al.

(10) Patent No.: US 12,797,001 B2
(45) Date of Patent: Nov. 17, 2026

(54) MONITORING EQUIPMENT, MONITORING SYSTEM, AND MONITORING METHOD

(71) Applicant: EDAN INSTRUMENTS, INC., Shenzhen (CN)

(72) Inventors: Ying Lei, Shenzhen (CN); Sihai Qiu, Shenzhen (CN); Dewei Chen, Shenzhen (CN); Dong Huang, Shenzhen (CN); Lin Tang, Shenzhen (CN); Huan Hu, Shenzhen (CN)

(73) Assignee: EDAN INSTRUMENTS, INC., Shenzhen (CN)

( * ) Notice: Subject to any disclaimer, the term of this patent is extended or adjusted under 35 U.S.C. 154(b) by 126 days.

(21) Appl. No.: 18/837,139

(22) PCT Filed: Sep. 15, 2022

(86) PCT No.: PCT/CN2022/119107
§ 371 (c)(1),
(2) Date: Aug. 8, 2024

(87) PCT Pub. No.: WO2023/159921
PCT Pub. Date: Aug. 31, 2023

(65) Prior Publication Data
US 2025/0134450 A1 May 1, 2025

(30) Foreign Application Priority Data
Feb. 28, 2022 (CN) ......................... 202210187584.2

(51) Int. Cl.
*A61B 5/00* (2006.01)
*A61B 5/0205* (2006.01)

(52) U.S. Cl.
CPC ........ *A61B 5/4362* (2013.01); *A61B 5/02055* (2013.01); *A61B 5/7445* (2013.01); *A61B 5/746* (2013.01)

(58) Field of Classification Search
None
See application file for complete search history.

(56) References Cited

U.S. PATENT DOCUMENTS

2003/0114779 A1* 6/2003 Paltieli ................ A61B 5/6826 600/588
2007/0191728 A1 8/2007 Shennib
(Continued)

FOREIGN PATENT DOCUMENTS

CA 2928062 A1 10/2017
CN 102473203 A 5/2012
(Continued)

OTHER PUBLICATIONS

First Office Action dated Oct. 25, 2025 of corresponding CN patent application No. 202210206211.5.
(Continued)

*Primary Examiner* — James B Hull
(74) *Attorney, Agent, or Firm* — Maschoff Brennan

(57) ABSTRACT

A monitoring equipment, a monitoring system and a monitoring method. The monitoring equipment includes a measurement unit that acquires monitoring parameters and a control unit connected with the measurement unit to determine current stage-of-labor progress based on types of acquired monitoring parameters, to thereby determine a monitoring object that includes a mother and a fetus and/or a newborn. A display unit is connected with the control unit to display corresponding monitoring parameters in areas corresponding to each monitoring object on a monitoring interface. The monitoring interface includes one or a plurality of a mother monitoring area, a fetus monitoring area and a newborn monitoring area. The measurement unit is provided in the monitoring equipment. The control unit determines the current stage-of-labor progress to determine a monitoring object. Monitoring parameters of each moni-
(Continued)

toring object are simultaneously displayed on the monitoring interface of the display unit, thereby improving the monitoring efficiency.

18 Claims, 10 Drawing Sheets

(56) References Cited

U.S. PATENT DOCUMENTS

| | | | | |
|---|---|---|---|---|
| 2012/0116194 | A1 | 5/2012 | Gross et al. | |
| 2015/0278178 | A1 | 10/2015 | Okuda et al. | |
| 2016/0374608 | A1 | 12/2016 | Dugan | |
| 2019/0117070 | A1 | 4/2019 | Muhsin et al. | |
| 2019/0133536 | A1 | 5/2019 | Roberts | |
| 2020/0121199 | A1 | 4/2020 | Freeman et al. | |
| 2021/0174917 | A1 | 6/2021 | Timme | |
| 2024/0415400 | A1* | 12/2024 | Krishnan ............. | A61B 5/7242 |

FOREIGN PATENT DOCUMENTS

| | | | |
|---|---|---|---|
| CN | 102499643 | A | 6/2012 |
| CN | 206852596 | U | 1/2018 |
| CN | 109419533 | A | 3/2019 |
| CN | 110558961 | A | 12/2019 |
| CN | 111212599 | A | 5/2020 |
| DE | 102011120406 | A1 | 6/2013 |
| JP | 2015-185125 | A | 10/2015 |
| RU | 170360 | U1 | 4/2017 |
| RU | 2756425 | C1 | 9/2021 |

OTHER PUBLICATIONS

First Office Action dated Nov. 29, 2025 of corresponding CN patent application No. 202210190159.9.

First Office Action dated Sep. 11, 2025 of corresponding CN patent application No. 202210187584.2.

International Search Report and Written Opinion of the International Searching Authority dated Dec. 7, 2022 as received in Application No. PCT/CN2022/119107.

CN Office Action dated Jul. 25, 2026 of patent application No. 2022102062115.

CN Office Action dated Jul. 22, 2026 of patent application No. 2022101875842.

CN Decision of Refusal dated Jul. 11, 2026 of patent application No. 202210190159.9.

* cited by examiner

MONITORING EQUIPMENT, MONITORING SYSTEM, AND MONITORING METHOD

TECHNICAL FIELD

The present disclosure relates to the technical field of monitoring equipments, in particular relates to a monitoring equipment, a monitoring system and a monitoring method.

TECHNICAL BACKGROUND

Under normal circumstances, after a newborn is delivered, it is necessary to monitor the physiological parameters of a mother and also to evaluate, resuscitate and monitor the newborn until two hours after delivery, and then the mother and the newborn are pushed out of the delivery room together. At present, the commonly used clinical method is to monitor the mother's parameters by fetal monitoring or patient monitoring, and to monitor the newborn by using a handheld oximeter, a neonatal warm radiation table, a neonatal monitoring equipment and other products. On the basis of this, medical staff must monitor the mother and the newborn by using multiple equipments, resulting in low monitoring efficiency.

SUMMARY OF THE INVENTION

In view of this, the embodiments of the present disclosure provide a monitoring equipment, a monitoring system and a monitoring method to solve the problem of low monitoring efficiency.

According to a first aspect, the embodiments of the present disclosure provide a monitoring equipment, comprising:

a measurement unit, configured to acquire monitoring parameters;

a control unit, connected with the measurement unit and configured to determine current stage-of-labor progress on the basis of types of the acquired monitoring parameters, so as to determine a monitoring object, wherein the monitoring object comprises a mother and a fetus and a newborn or a mother and a fetus; and a display unit, connected with the control unit and configured to display corresponding monitoring parameters in areas corresponding to each monitoring object on a monitoring interface, wherein the monitoring interface comprises one or a plurality of a mother monitoring area, a fetus monitoring area and a newborn monitoring area.

According to the monitoring equipment provided by the embodiments of the present disclosure, the measurement unit for acquiring monitoring parameters is provided in the monitoring equipment, and the control unit is configured to determine the current stage-of-labor progress so as to determine a monitoring object, and monitoring parameters of each monitoring object are simultaneously displayed on the monitoring interface of the display unit, thereby improving the monitoring efficiency.

According to a second aspect, the embodiments of the present disclosure provide a monitoring system, comprising:

the monitoring equipment according to the first aspect or any embodiment of the first aspect;

one or a plurality of neonatal parameter measuring equipment, connected with the monitoring equipment;

a monitoring workstation, the monitoring workstation being respectively communicationally connected with the monitoring equipment and the one or a plurality of neonatal parameter measuring equipment.

In the monitoring system provided by the embodiments of the present disclosure, the neonatal parameter measuring equipment can be directly connected with the monitoring equipment, and can also be communicationally connected to the monitoring equipment through the monitoring workstation, so as to meet the communicational connection requirements of different equipments and expand the range of application scenarios.

According to a third aspect, the embodiments of the present disclosure provide a monitoring method, comprising:

displaying maternal physiological parameters and fetal physiological parameters respectively on a mother monitoring area and a fetus monitoring area of a monitoring interface;

determining current stage-of-labor progress on the basis of types of acquired monitoring parameters;

determining monitoring objects on the basis of the current stage-of-labor progress, and displaying corresponding monitoring parameters in areas corresponding to each monitoring object on the monitoring interface, wherein the monitoring interface comprises one or a plurality of the mother monitoring area, the fetus monitoring area and a newborn monitoring area.

According to the monitoring method provided by the embodiments of the present disclosure, the maternal physiological parameters and the fetal physiological parameters are initially displayed at the same time, and the corresponding displayed contents would be switched on the monitoring interface along with the progress of stage-of-labor, that is, the specific displayed contents are related to the monitoring object determined in the current stage-of-labor process, so that each monitoring object can be monitored simultaneously on the same monitoring interface without the need to switch between different monitoring equipments, so that the monitoring efficiency is improved.

BRIEF DESCRIPTION OF DRAWINGS

In order to explain the technical scheme in the specific embodiments of the present disclosure or in the prior art more clearly, the appended drawings needed in the description of the specific embodiments or the prior art will be briefly introduced below. Apparently, the drawings described in the following description only represent some embodiments of the present disclosure, and other drawings can be obtained by a person skilled in the art according to these drawings without creative work.

DETAILED DESCRIPTION OF SPECIFIC EMBODIMENTS

In order to make the purpose, technical scheme and advantages of the embodiments of the disclosure more clearly understood, the technical scheme in the embodiments of the present disclosure will be described clearly and completely with reference to the appended drawings. Apparently, the described embodiments only represent part of the embodiments of the present disclosure, not all of them. On the basis of the embodiments described in the present disclosure, all other embodiments obtainable by those skilled in the art without creative work belong to the protection scope of the present disclosure.

Figure 1:
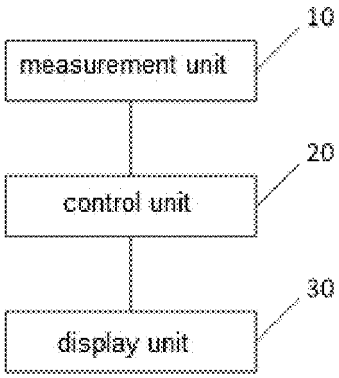
FIG. 1 is a structural block diagram of a monitoring equipment according to an embodiment of the present disclosure.

The embodiments of the present disclosure provide a monitoring equipment, as shown in FIG. 1, the monitoring equipment comprises a measurement unit 10, a control unit 20 and a display unit 30. The control unit 20 is connected with the measurement unit 10, and the display unit 30 is connected with the control unit 20. The monitoring equipment is configured to monitor the respective monitoring objects at the same time during a process of stage-of-labor progress, for example, said monitoring objects include a mother and a fetus at the beginning of labor; when fetuses have partially been delivered, said monitoring objects include a mother, a fetus and a newborn; when fetuses have all been delivered, said monitoring objects include a mother and newborns. On the basis of this, on a monitoring interface of the monitoring equipment, along with the progress of stage-of-labor, the corresponding monitoring parameters are displayed in the respective monitoring areas corresponding to each monitoring object on the monitoring interface. The monitoring parameters of each monitoring object are not limited herein, and may be set or configured according to actual needs.

Specifically, the measurement unit 10 is configured to obtain monitoring parameters, which comprise monitoring parameters of one or a plurality of monitoring object, and each monitoring object may have one or a plurality of kind of monitoring parameter. The acquisition of monitoring parameters may be fully measured by the measuring unit 10, or may be partially measured by the measurement unit 10, and partially obtained by the measurement unit 10 from other measurement equipment. For example, the monitoring equipment is a maternal-fetal monitor, which comprises a measurement unit 10 for measuring maternal monitoring parameters and fetal monitoring parameters, and neonatal monitoring parameters are acquired from the outside by the measurement unit 10; the acquisition of neonatal monitoring parameters may be obtained by accessory modules or other connected neonatal monitoring equipments, etc., which is no limited herein, and may be set according to actual needs.

The control unit 20 is configured to determine current stage-of-labor progress on the basis of types of the acquired monitoring parameters, so as to determine a monitoring object. The types of monitoring parameters comprise maternal physiological parameters, fetal physiological parameters or neonatal monitoring parameters. The control unit 20 determines the type of monitoring parameter according to a source of each monitoring parameter; or determines the type of monitoring parameter according to an identification sign of each monitoring parameter. After determining the type of each monitoring parameter, the control unit 20 may determine the current stage-of-labor progress, that is, whether it is an initial stage of delivery, a stage that fetuses have partially been delivered, or a stage that fetuses have all been delivered. On the basis of this, the control unit 20 adjusts a layout of the monitoring interface to simultaneously display the monitoring parameters of each monitoring object on the monitoring interface.

The display unit 30 is also configured to display the corresponding monitoring parameters in areas corresponding to each monitoring object on the monitoring interface. Wherein, the monitoring interface comprises one or a plurality of a mother monitoring area, a fetus monitoring area and a newborn monitoring area. The control unit 20 adjusts the layout of the monitoring interface on the basis of changes of the monitoring objects, and accordingly, the display unit 30 displays corresponding monitoring parameters in areas corresponding to each monitoring object.

Figure 2:
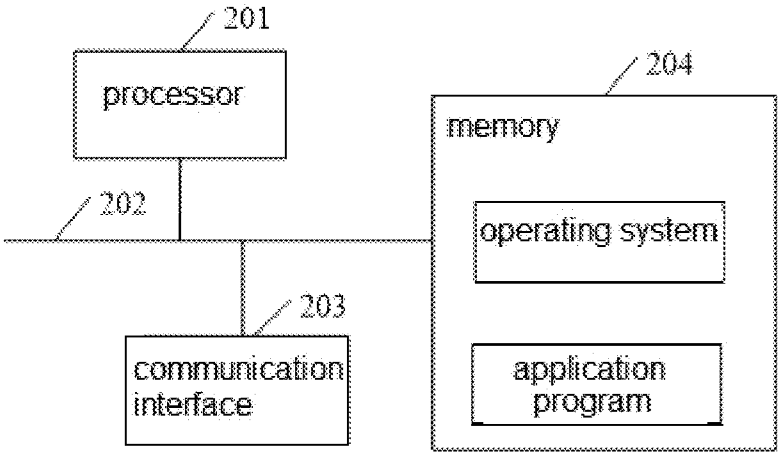
FIG. 2 is a structural block diagram of a control unit according to an embodiment of the present disclosure.

Referring to FIG. 2, which is a schematic structural diagram of a control unit 20 provided by an optional embodiment of the present disclosure. As shown in FIG. 2, the control unit 20 may comprise one or a plurality of processor 201, such as a CPU (Central Processing Unit), one or a plurality of communication interface 203, a memory 204 and one or a plurality of communication bus 202. The communication bus 202 is configured for realizing communicational connection between these components. The communication interface 203 may comprise a display and a keyboard, and optionally the communication interface 203 may also comprise a standard wired interface and a standard wireless interface. The memory 204 may be a Random Access Memory (RAM, which is volatile) or a non-volatile memory, such as one or a plurality of disk memory. The memory 204 may optionally be one or a plurality of storage device located remotely from the aforementioned processor 201. Wherein the processor 201 may be combined with the apparatus described with reference to FIG. 16, an application program is stored in the memory 204, and the processor 201 calls the program codes thereof stored in the memory 204 for executing any of the above method steps.

The communication bus 202 may be a peripheral component interconnect (PCI) bus or an extended industry standard architecture (EISA) bus, etc. The communication bus 202 may be divided into an address bus, a data bus, a control bus and the like. For convenience of representation, only a thick line is used in FIG. 2, but it does not mean that there is only one bus or only one type of bus.

The memory 204 may comprise a volatile memory, such as a random-access memory (RAM); The memory may also comprise non-volatile memory, such as flash memory, hard disk drive (HDD) or solid-state drive (SSD). The memory 204 may also comprise a combination of the above kinds of memories.

The processor 201 may be a central processing unit (CPU), a network processor (NP) or a combination of CPU and NP.

The processor 201 may further comprise a hardware chip. The hardware chip may be an application-specific integrated circuit (ASIC), a programmable logic device (PLD) or a combination thereof. The PLD may be a complex programmable logic device (CPLD), a field-programmable gate array (FPGA), a generic array logic (GAL) or any combination thereof.

Optionally, the memory 204 is also configured to store program instructions. The processor 201 may call the program instructions to implement the monitoring method as described in embodiments of the present application.

It should be noted that the monitoring equipment in the embodiments of the present disclosure may be a monitoring equipment having a neonatal monitoring function, or it may be connected to an external neonatal monitoring module through an interface, or it may obtain the physiological parameters, monitoring events, etc. of the newborn from other devices, which is no limited herein. For example, the monitoring equipment in the embodiments of the present disclosure is a maternal-fetal monitor, and monitoring results of a mother, a fetus and a newborn can be displayed on the maternal-fetal monitor at the same time. Specifically, a neonatal parameter monitor sends the physiological parameters of a newborn to the maternal-fetal monitor, so that the maternal-fetal monitor can acquire the physiological parameters of the target newborn, thereby realizing monitoring of the fetus, the mother and the target newborn at the same time. Wherein, the neonatal parameter monitor may be an independent monitoring equipment or an accessory module adapted to the maternal-fetal monitoring equipment, wherein the accessory module is configured to monitor a newborn.

In some embodiments alternative to this embodiment, the measurement unit 10 comprises a maternal parameter measuring apparatus, a fetal parameter measuring apparatus and a neonatal parameter measuring apparatus. The maternal parameter measuring apparatus is configured to acquire monitoring parameters of the mother, the fetal parameter measuring apparatus is configured to acquire monitoring parameters of the fetus, and the neonatal parameter measuring apparatus is configured to acquire monitoring parameters of the newborn. For example, the monitoring parameters of the mother comprise: uterine contraction pressure, uterine myoelectricity, intrauterine pressure, ECG, respiration, blood pressure, blood oxygen, pulse, body temperature and so on; the monitoring parameters of the fetus comprise: fetal heart rate, fetal ECG and so on; the monitoring parameters of the newborn comprise: neonatal blood oxygen, respiration, body temperature, ECG, pulse, blood pressure, etc., which at least supports the measurement of neonatal blood oxygen parameter. Of course, the above-mentioned monitoring parameters are only examples, and they may be set or adjusted according to actual needs.

Wherein, the neonatal parameter measuring apparatus may be implemented by an accessory module or a built-in neonatal parameter measuring module.

Specifically, the newborn parameter measuring apparatus comprises one or a plurality of accessory interface, the accessory interface is configured to be connected to a neonatal parameter measuring accessory for measuring the monitoring parameters of a newborn. Wherein, a specific type of the neonatal parameter measurement accessory may be selected according to actual needs.

Alternatively, the neonatal parameter measuring apparatus comprises one or a plurality of neonatal parameter measuring module arranged within the monitoring equipment, and the neonatal monitoring parameters can be directly measured by this built-in neonatal parameter measuring module.

The neonatal parameter measuring apparatus is used in postpartum monitoring mode, that is, after the newborn is born, some parameters need to be monitored, and the main monitoring parameter of the newborn is blood oxygen. The blood oxygen parameter may be measured by a built-in neonatal blood oxygen module within the maternal-fetal monitor; or the blood oxygen parameter may be monitored by another neonatal monitoring equipment, and the neonatal monitoring equipment transmits monitoring data to the maternal-fetal monitor in a wired or wireless way; it may also be monitored by an accessory module, at this time, an accessory interface is provided on the maternal-fetal monitor, and when the accessory module is connected to the accessory interface, the data of the accessory module is transmitted to the maternal-fetal monitor through the physical interface. After the accessory module is unplugged from the interface slot, the accessory module may be used as an independent device to monitor a newborn independently.

It should be noted that for the maternal parameter measuring apparatus and the fetal parameter measuring apparatus, the measurement of the maternal monitoring parameter and the fetal monitoring parameter may also be implemented by means of external accessory modules, which is no limitation herein, and may be set according to actual needs.

when the control unit recognizes that a different type of accessory module (such as the above-mentioned blood oxygen module) is plugged in and becomes accessible, the control unit controls a display interface of the display unit to automatically adjust the sizes and positions of the areas corresponding to each monitoring object according to the newly accessible parameter types and the number of parameters for each type, so as to present an optimal viewing effect. Wherein, optionally, different parameters would be distinguished from each other in one or more ways such as colors, characters and pictures, which is convenient for a user to view. Each monitoring area may contain multiple sub-windows, and contents of the sub-windows comprise parameter values, trend charts, parameter tables, alarm information, alarm records, etc. For example, when medical staff wants to monitor a certain monitoring object in detail, they may select an area corresponding to this monitoring object on the monitoring interface so as to enter a detailed monitoring interface of this monitoring object.

Figure 3:
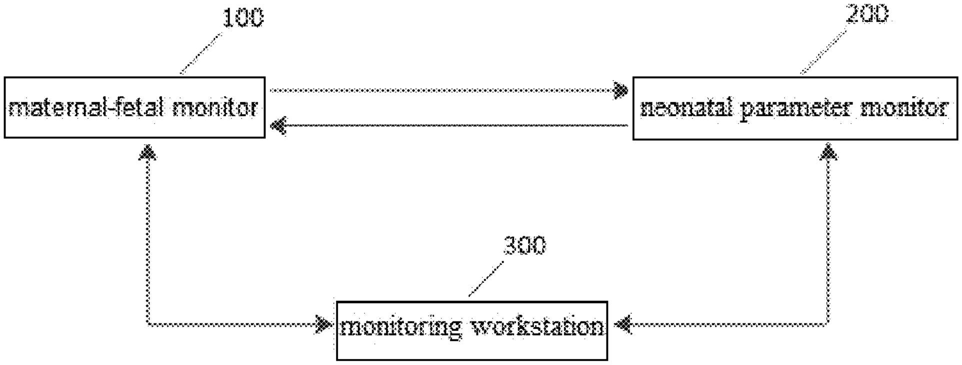
FIG. 3 is a structural block diagram of a monitoring system according to an embodiment of the present disclosure.

The embodiments of the present disclosure also provide a monitoring system, as shown in FIG. 3, the monitoring system comprises a maternal-fetal monitor, a neonatal parameter monitor and a monitoring workstation. Specifically, the neonatal parameter monitor sends monitoring data collected for a newborn to the maternal-fetal monitor, either directly or indirectly through the monitoring workstation, and so on. Accordingly, the maternal-fetal monitor may also send data to the neonatal parameter monitor.

For example, when the delivery has not yet begun, a mother monitoring area and a fetus monitoring area are simultaneously displayed on the maternal-fetal monitor; in the case of multiple fetuses, the mother monitoring area, a newborn monitoring area and the fetus monitoring area can be simultaneously displayed on the maternal-fetal monitor; and when the fetuses have all been delivered, the mother monitoring area and the newborn monitoring area are simultaneously displayed on the maternal-fetal monitor.

Of course, FIG. 3 is only an optional embodiment of the monitoring system, and the protection scope of the present disclosure is not limited to this.

According to the embodiments of the present disclosure, an embodiment of a monitoring method is provided. It should be noted that the steps shown in the flowchart of the appended drawings may be executed in a computer system such as with a set of computer-executable instructions, and although a logical order is shown in the flowchart, in some cases, the steps shown or described may be executed in an order different from here.

Figure 4:
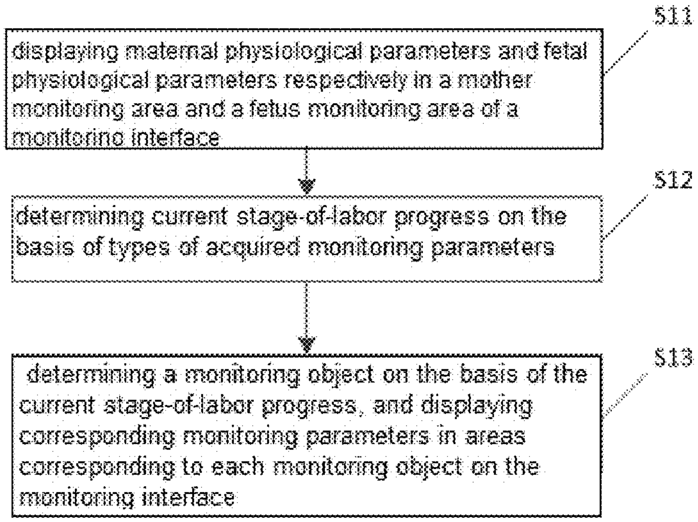
FIG. 4 is a flowchart of a monitoring method according to an embodiment of the present disclosure.

In this embodiment, a monitoring method is provided, which may be applied to the above monitoring equipment. FIG. 4 is a flowchart of the monitoring method according to the embodiments of the present disclosure, as shown in FIG. 4, the flow comprises the following steps:

S11, displaying maternal physiological parameters and fetal physiological parameters respectively in a mother monitoring area and a fetus monitoring area of a monitoring interface.

The maternal physiological parameters and the fetal physiological parameters may be measured by the monitoring equipment, and on the basis of this, the maternal physiological parameters and the fetal physiological parameters are displayed on a monitoring interface of the monitoring equipment respectively. The monitoring interface comprises a mother monitoring area and a fetus monitoring area.

The specific parameters included in the maternal physiological parameters are set according to the actual monitoring requirements, and the maternal physiological parameters displayed in the mother monitoring area for different mothers may be the same or different. For example, it may be configured on the monitoring equipment. The specific parameters included in the fetal physiological parameters are also set according to the actual monitoring requirements. The fetal physiological parameters displayed in the fetus monitoring area for different fetuses may be the same or different.

If the monitoring equipment is not specifically configured with maternal physiological parameters or fetal physiological parameters, the default parameters of maternal physiological parameters are displayed in the mother monitoring area or the default parameters of fetal physiological parameters are displayed in the fetus monitoring area.

S12, determining current stage-of-labor progress on the basis of types of acquired monitoring parameters.

After obtaining the monitoring parameters, the monitoring equipment may determine a type of each monitoring parameter according to the source or the identification sign of each monitoring parameter, and then use the types of the respective monitoring parameters to determine the current stage-of-labor progress. For details, please refer to the relevant description in the embodiments of the monitoring equipment above, which will not be repeated herein.

S13, determining a monitoring object on the basis of the current stage-of-labor progress, and displaying corresponding monitoring parameters in areas corresponding to each monitoring object on the monitoring interface.

Wherein the monitoring interface comprises one or a plurality of the mother monitoring area, the fetus monitoring area and a newborn monitoring area.

After determining the current stage-of-labor progress, the monitoring equipment may determine the monitoring objects, and then display the monitoring parameters of each monitoring object in the respective areas of the monitoring interface. For details, please refer to the relevant description in the embodiments of the monitoring equipment above, which will not be repeated herein.

In the monitoring method provided by this embodiment, the maternal physiological parameters and the fetal physiological parameters are initially displayed at the same time, and the corresponding displayed contents would be switched on the monitoring interface along with the progress of stage-of-labor, that is, the specific displayed contents are related to the monitoring object determined in the current stage-of-labor process, so that each monitoring object can be monitored simultaneously on the same monitoring interface without the need to switch between different monitoring equipments, so that the monitoring efficiency is improved.

In some optional embodiments of this general embodiment, if the current stage-of-labor progress is that one or more fetuses have all been delivered, the monitoring objects are a mother and one or more newborns, on the basis of this, displaying corresponding monitoring parameters in areas corresponding to each monitoring object on the monitoring interface in step S13 comprises:

(1) displaying neonatal physiological parameters in the newborn monitoring area;

(2) displaying maternal physiological parameters in the mother monitoring area.

Specifically, if there is one newborn, the monitoring interface comprises one newborn monitoring area, and if there are two newborns, the monitoring interface comprises two newborn monitoring areas. That is, the number of the newborn monitoring areas is the same as that of the newborns. According to the number of the newborns, the monitoring equipment lays out the monitoring interface to obtain each newborn monitoring area.

For example, the monitoring equipment firstly determines one area of the monitoring interface as a mother monitoring area, and then divides the rest of the areas of the monitoring interface into newborn monitoring areas having the same number as that of the newborns.

After a layout of the monitoring interface is completed, the maternal physiological parameters are displayed in the mother monitoring area and the neonatal physiological parameters are displayed in each newborn monitoring area.

when the fetuses have all been delivered, the monitoring interface comprises a mother monitoring area and one or more newborn monitoring areas, and the corresponding physiological parameters are displayed in each area so as to monitor each monitoring object at the same time.

In other optional embodiments of this general embodiment, if the current stage-of-labor progress is that fetuses have partially been delivered, the monitoring objects are a mother, a newborn and a fetus, on the basis of this, displaying corresponding monitoring parameters in areas corresponding to each monitoring object on the monitoring interface in step S13 comprises:

(1) displaying neonatal physiological parameters in the newborn monitoring area;

(2) displaying fetal physiological parameters in the fetus monitoring area;

(3) displaying maternal physiological parameters in the mother monitoring area.

Figure 5A:
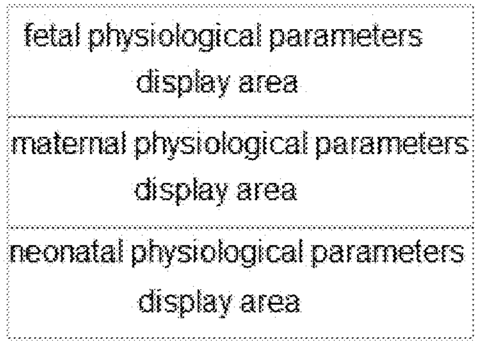
FIGS. 5*a*-5*c* are schematic diagrams of a monitoring interface according to embodiments of the present disclosure.
Figure 5B:
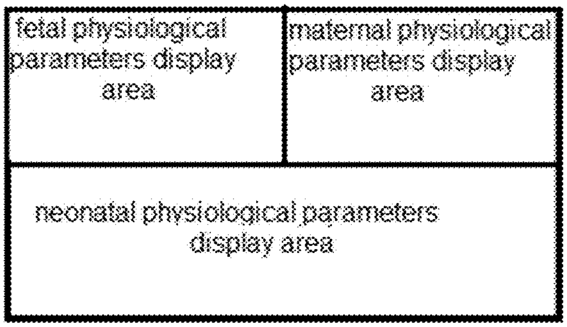
Figure 5C:
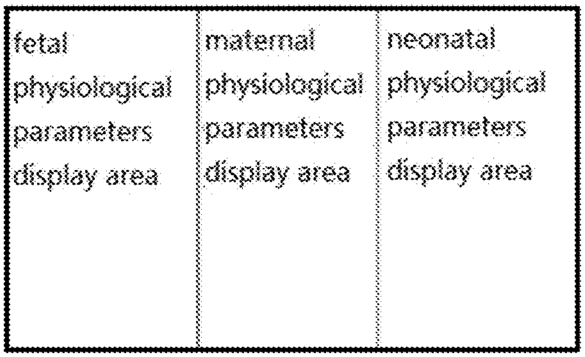

Specifically, when there are at least two fetuses, a fetus and a newborn would be present at the same time because of a delivery sequence of the at least two fetuses. Therefore, the monitoring interface would comprise the newborn monitoring area and the fetus monitoring area. Of course, the number of the newborn monitoring areas and the number of the fetus monitoring areas are respectively consistent with the corresponding number of the newborns and the corresponding number of the fetuses.

when fetuses have partially been delivered, the mother, fetus and newborn are monitored at the same time, which improves the monitoring efficiency. Taking one fetus and one newborn as an example, display modes of the monitoring interface are shown in FIG. 5*a*, FIG. 5*b* or FIG. 5*c*. It should be noted that FIGS. 5*a*-5*c* are only some feasible display modes, but they do not limit the protection scope of the present disclosure, and the interface layout may be made according to actual needs.

As an optional embodiment of this general embodiment, when fetuses have all been delivered, displaying corresponding monitoring parameters in areas corresponding to each monitoring object on the monitoring interface in step S13 further comprises: displaying the fetus monitoring area on the monitoring interface. After the fetuses are all delivered, the fetal physiological parameters disappear, that is, the currently-detected fetal physiological parameters in the fetus monitoring area disappear, but the fetus monitoring area is still displayed, so that users can review the fetal physiological parameters conveniently.

when the fetuses have all been delivered, the fetus monitoring area is retained while displaying the physiological parameters of the newborn and the mother, so as to facilitate a subsequent review of the parameters.

Optionally, after a certain currently-detected monitoring parameter disappears, the corresponding independent monitoring area would not disappear, which is convenient for users to review the monitoring data and to operate for generating independent monitoring reports, such as a maternal monitoring record, fetal monitoring reports and neonatal monitoring reports, etc.

Figure 6:
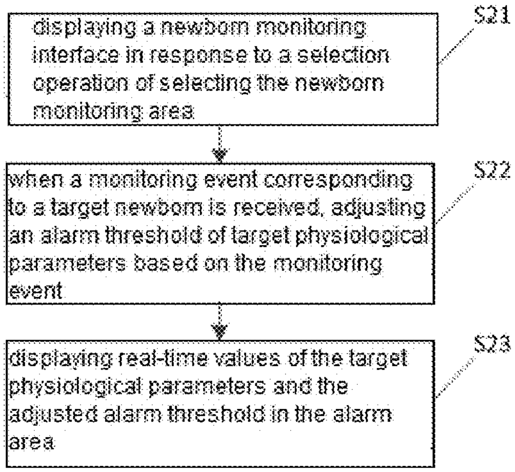
FIG. 6 is a flowchart of a monitoring method according to an embodiment of the present disclosure.

In this embodiment, a monitoring method is provided, which may be applied to the above monitoring equipment. FIG. 6 is a partial flow chart of the monitoring method according to the embodiments of the present disclosure, as shown in FIG. 6, which is described on the basis of the monitoring method shown in FIG. 4, it comprises the following steps:

S21, displaying a newborn monitoring interface in response to a selection operation of selecting the newborn monitoring area.

Figure 7:
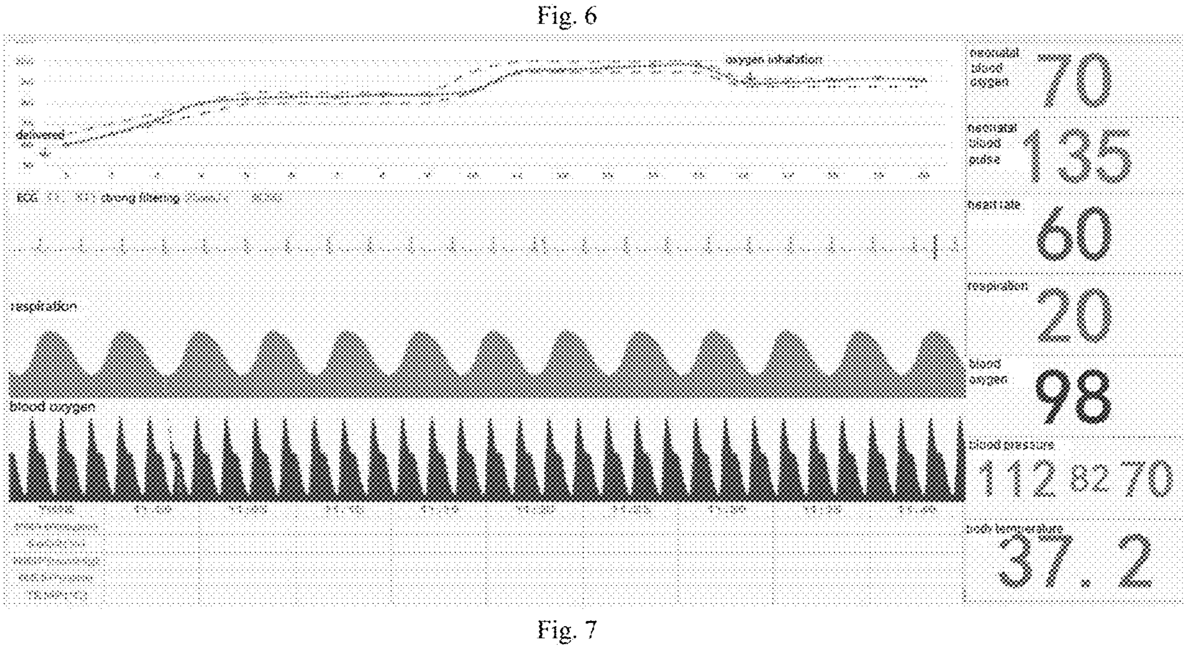
FIG. 7 is a schematic diagram of a newborn monitoring interface according to an embodiment of the present disclosure.

Wherein, the newborn monitoring interface comprises an alarm area.

when the medical staff needs to emphasize monitoring the newborn, they select the newborn monitoring area, and the monitoring equipment will switch to the newborn monitoring interface. The newborn monitoring interface is configured to display the alarm area, that is, to display an alarm threshold and a comparison result between a real-time value of the target physiological parameter and a corresponding alarm threshold. Alternatively, as shown in FIG. 7, the newborn monitoring interface should comprise a monitoring parameter display area for displaying the real-time values of various monitoring parameters of a target newborn.

S22, when a monitoring event corresponding to a target newborn is received, adjusting an alarm threshold of target physiological parameters based on the monitoring event.

As for a manner in which a monitoring event is received, please refer to the above, due to different physiological parameters are affected by different monitoring events, when the monitoring equipment receives a monitoring event corresponding to a target newborn, it firstly determines the target physiological parameters corresponding to the monitoring event, and then adjusts the alarm threshold of the target physiological parameters. The correspondence relationship between monitoring events and physiological parameters may be stored in the monitoring equipment in advance. For example, the target physiological parameters related to monitoring event A comprise a1, a2 and a3; the target physiological parameters related to monitoring event B comprise b1 and b2; the target physiological parameters related to monitoring event C comprise a1 and b2. On the basis of this, the monitoring equipment may determine the target physiological parameters corresponding to each monitoring event by using this correspondence relationship.

After the target physiological parameters are determined, the monitoring equipment queries out an alarm threshold corresponding to the target physiological parameters, and then adjusts the target physiological parameters on the basis of the acquired monitoring event. As mentioned above, when the monitoring event A occurs, it comprises an increase of alarm thresholds for the target physiological parameters of a1, a2 and a3; when the monitoring event B occurs, it comprises a decrease of alarm thresholds for the target physiological parameters of b1 and b2.

Wherein, an adjustment of the alarm threshold may be an adjustment of the alarm threshold within a duration after an occurrence of the monitoring event, and after the end of this duration, the adjusted alarm threshold is restored to a normal alarm threshold corresponding to a post-delivery period; it may also adjust the alarm threshold corresponding to the entire post-delivery period after a monitoring event, and so on. There is no specific limitation on it, and it may be set according to actual needs.

S23, displaying real-time values of the target physiological parameters and the adjusted alarm threshold in the alarm area.

The acquisition of the real-time values of the target physiological parameters may be obtained by measuring through the monitoring equipment or be obtained by the monitoring equipment from other devices, and so on. The monitoring equipment simultaneously displays the real-time values of the target physiological parameters and the adjusted alarm threshold in the alarm area, so as for the user to intuitively understand the current monitoring situation. Furthermore, the monitoring equipment compares the real-time value of the target physiological parameter with the adjusted alarm threshold, and determines a relationship between the real-time value of the target physiological parameter and the alarm threshold, thus determining a comparison result.

For example, when the real-time value of the target physiological parameter exceeds the adjusted alarm threshold, the target physiological parameter may be represented by a first identifier; when the real-time value of the target physiological parameter is less than the adjusted alarm threshold, the target physiological parameter is represented by a second identifier; when the real-time value of the target physiological parameter is determined to be normal, the target physiological parameter is represented by a third identifier, and so on. Wherein, each identifier may be in different colors, different line types and so on.

Of course, the specific display form of the alarm area is not limited herein, and it may be set according to actual needs.

According to the monitoring method provided by the embodiments of the present disclosure, when a corresponding monitoring event happens to a target newborn, the monitoring event would affect a value size of an alarm threshold, so that the alarm threshold is adjusted on the basis of the monitoring event, thereby ensuring the reliability of newborn monitoring.

Figure 8:
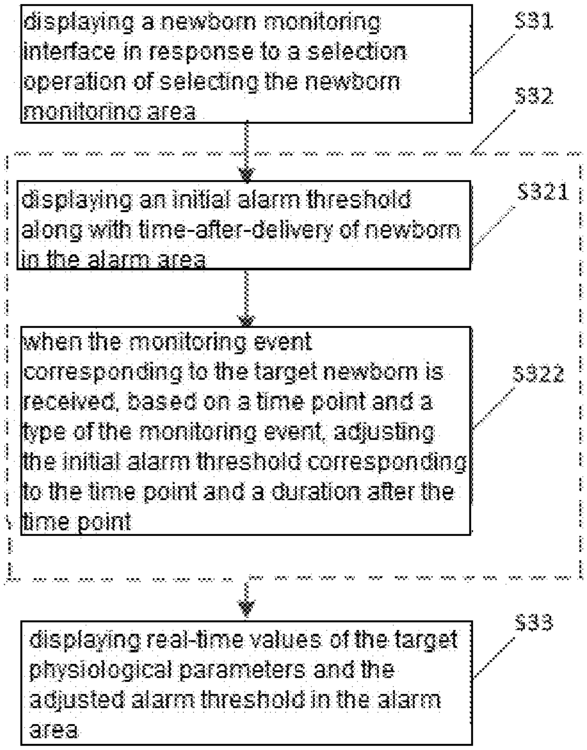
FIG. 8 is a flowchart of a monitoring method according to an embodiment of the present disclosure.

In this embodiment, a monitoring method is provided, which may be applied to the above monitoring equipment. FIG. 8 is a flowchart of the monitoring method according to the embodiments of the present disclosure. This embodiment is described in further detail on the basis of the embodiment shown in FIG. 6. As shown in FIG. 8, the flow comprises the following steps:

S31, displaying a newborn monitoring interface in response to a selection operation of selecting the newborn monitoring area.

Wherein the newborn monitoring interface comprises an alarm area.

Please refer to step S21 of the embodiment shown in FIG. 6 for details, which will not be repeated herein.

S32, when a monitoring event corresponding to a target newborn is received, adjusting an alarm threshold of target physiological parameters based on the monitoring event.

Specifically, S32 comprises:

S321, displaying an initial alarm threshold along with time-after-delivery of newborn in the alarm area.

Figure 9A:
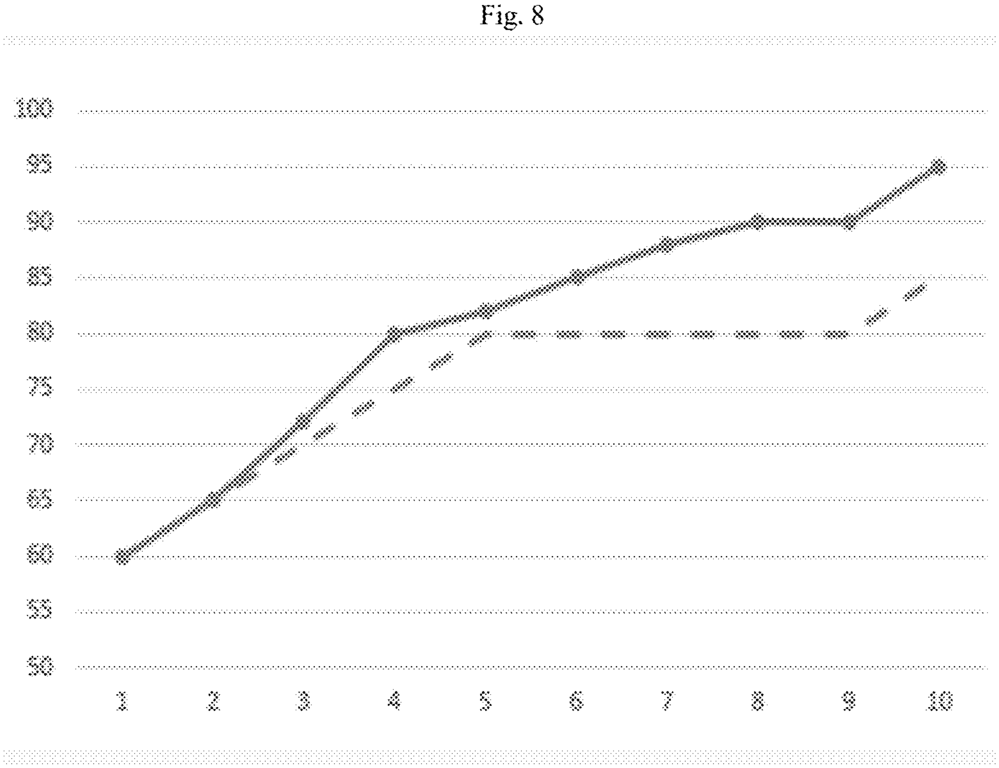
FIGS. 9*a*-9*b* are schematic diagrams of an initial alarm threshold according to embodiments of the present disclosure.

As mentioned above, the initial alarm threshold changes along with time-after-delivery of the newborn, so the initial alarm threshold displayed in the alarm area of the monitoring equipment changes along with time-after-delivery of the newborn. It should be noted that the time-after-delivery herein does not refer to the delivery time of the newborn, but refers to the time after delivery. For example, as shown in FIG. 9*a*, the abscissa is the time-after-delivery of the newborn, the ordinate is an amplitude of the alarm threshold, the solid line is an upper limit of the alarm threshold, and the dotted line is a lower limit of the alarm threshold.

Figure 9B:
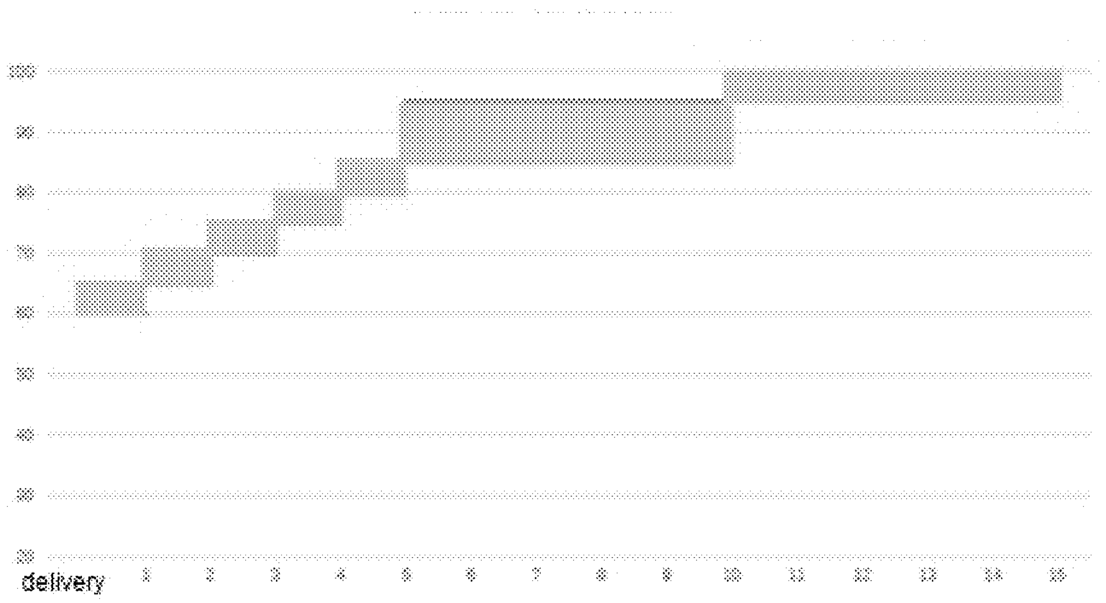

Alternatively, except for presenting the initial alarm threshold in a form of curve, it may also be expressed in a form of color block. For example, as shown in FIG. 9*b*, the abscissa is the time-after-delivery of newborn, the ordinate is an amplitude of the alarm threshold, an upper surface of color block is an upper limit of the alarm threshold, and a lower surface of color block is a lower limit of the alarm threshold.

S322, when the monitoring event corresponding to the target newborn is received, based on a time point and a type of the monitoring event, adjusting the initial alarm threshold corresponding to the time point and a duration after the time point.

when the monitoring equipment receives the monitoring event, the monitoring equipment records the time point when the monitoring event occurs, that is, records a target time-after-delivery corresponding to an occurrence of the monitoring event. On the basis of the way of adjustment described above, the monitoring equipment adjusts the initial alarm threshold corresponding to the time point and a duration after the time point on the basis of the type of the monitoring event. Wherein, the adjustment may be made only for the initial alarm threshold at the target time-after-delivery and for a duration thereafter. For example, if the target time-after-delivery is 5 minutes, that is, a monitoring event occurs at 5 minutes after the target newborn is delivered, and said duration is 10 minutes, then the monitoring equipment would adjust the initial alarm threshold within 5-15 minutes after delivery. Alternatively, all initial alarm thresholds subsequent to the target time-after-delivery may be adjusted.

Figure 10:
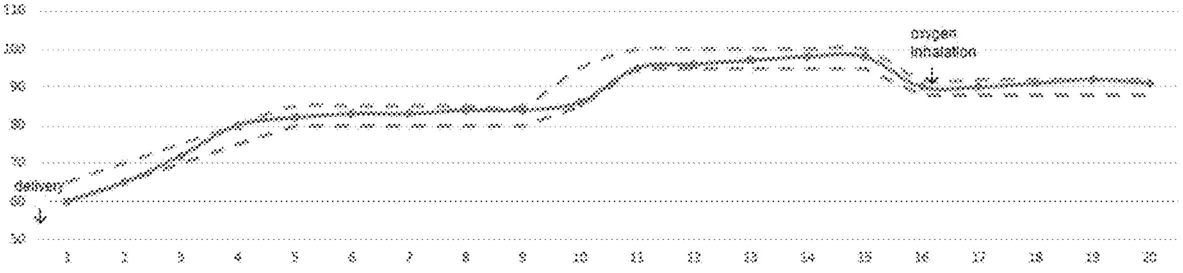
FIG. 10 is a schematic diagram of an adjusted alarm threshold according to an embodiment of the present disclosure.

As shown in FIG. 10, the alarm area displays the adjusted alarm threshold. Taking a target physiological parameter being blood oxygen as an example, under normal circumstances, the upper and lower limits of the blood oxygen value increase along with the increase of the time-after-delivery, but after the oxygen inhalation event, the upper and lower limits of the blood oxygen value would decrease for a duration, and then gradually increase to a stable level.

Optionally, the initial alarm threshold may be expressed in a form of curve, or in a form of color block, or in other ways, and so on, and there is no limitation on it herein. Wherein, the initial alarm threshold comprises an upper alarm limit and/or a lower alarm limit. On the basis of this, step S323 mentioned above may comprise: displaying the adjusted upper alarm limit and/or the adjusted lower alarm limit in the alarm area, and marking the type of the monitoring event in a zone of the alarm area corresponding to the time point.

As shown in FIG. 7 and FIG. 10, the type of the monitoring event is marked in a zone of the alarm area corresponding to the time point, that is, it is marked what kind of monitoring event occurs. Specifically, at a position on an alarm curve corresponding to the time point when the monitoring event occurs, an arrow is generated and the type of the monitoring event is displayed.

The type of the monitoring event is further displayed in the alarm area, so that medical staff can understand the reason for the change of alarm threshold at this time point.

S33, displaying real-time values of the target physiological parameters and the adjusted alarm threshold in the alarm area.

For details, please refer to step S23 of the embodiment shown in FIG. 6, which is not repeated herein.

As a specific application example of this embodiment, the target physiological parameter comprises blood oxygen, and on the basis of this, the step S33 mentioned above further comprises displaying a curve of the blood oxygen and a curve of the alarm threshold in the alarm area.

when the monitoring equipment obtains the time-after-delivery, it would adjust the neonatal blood oxygen alarm threshold according to the time-after-delivery, wherein the alarm threshold and the neonatal blood oxygen value will both be displayed on the newborn monitoring interface. After the newborn is delivered, a range of normal blood oxygen is different according to the time-after-delivery, and the lower limits of blood oxygen for 1-10 minutes are different. A blood oxygen situation of the newborn and whether it exceeds the alarm threshold can be directly observed on this newborn monitoring interface.

At the same time, when the monitoring equipment acquires different records of monitoring events, the upper and lower limits of blood oxygen alarm threshold would be adjusted accordingly. For example, in clinical practice, all newborns who take oxygen inhalation must be monitored for blood oxygen saturation, when a sign of oxygen inhalation event is acquired, the upper and lower limits of blood oxygen alarm threshold of the monitoring equipment should be adjusted to 88%-92%, so as to reduce the risk of blindness caused by retinopathy caused by long-term exposure of a newborn to oxygen-enriched environment.

According to the monitoring method provided by the embodiments of the present disclosure, the alarm threshold is adjusted at the time point when the monitoring event occurs and for a duration thereafter, so that the adjustment of initial alarm thresholds of all time is avoided, the data processing amount is reduced, the reliability of monitoring is improved, and the adjusted alarm threshold is displayed in the alarm area in real time, so that medical staff can know the current monitoring situation in time.

Figure 11:
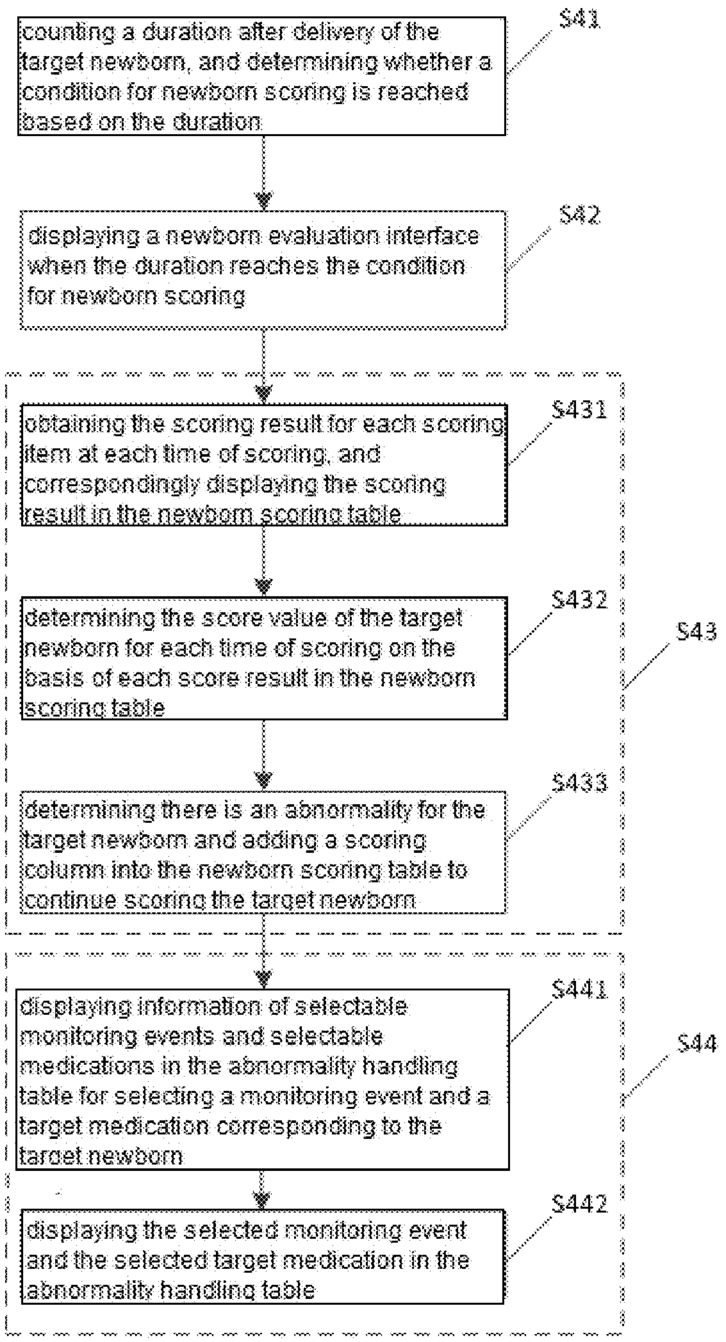
FIG. 11 is a flowchart of a monitoring method according to an embodiment of the present disclosure.

In this embodiment, a monitoring method is provided, which may be applied to the above monitoring equipment. What has been described above is the way to adjust the alarm threshold of the target physiological parameters on the basis of a monitoring event. In this embodiment, the contents related to newborn scoring are described in detail. There is no distinction of order of precedence between the steps described in this embodiment and those described above. The process is to monitor the newborn normally, and when a duration after delivery reaches a condition for newborn scoring, a newborn evaluation interface will be displayed to score the newborn. If it is determined that the newborn is abnormal on the basis of the score, it would send out an alert that it is necessary to treat the newborn with a corresponding monitoring event. Correspondingly, the monitoring equipment may receive the monitoring event of the target newborn, and then adjust the alarm threshold of the target physiological parameters. Specifically, FIG. 11 is a flowchart of a monitoring method according to an embodiment of the present disclosure. In this embodiment, only the detailed process of newborn scoring is described, and the adjustment mode of the alarm threshold is not repeatedly described herein. As shown in FIG. 11, the process comprises the following steps:

S41, counting a duration after delivery of the target newborn, and determining whether a condition for newborn scoring is reached based on the duration.

A post-delivery label may be set on the newborn monitoring interface, and when the medical staff triggers the post-delivery label, the monitoring equipment begins to record the duration after delivery; Alternatively, the monitoring equipment may also get to know the duration after delivery of the target newborn in other ways, so as to perform counting on the duration after delivery.

Newborn scoring, namely Apgar evaluation, stipulates that the target newborn needs to be scored on the basis of the physiological parameters and physical condition of the target newborn at intervals starting from delivery. For example, under normal circumstances, Apgar evaluation is required within 10 minutes after birth of a newborn and is needed to be done every 5 minutes. If the evaluation results are normal, the monitoring equipment records the information and continue to do routine monitoring of the target newborn; if the Apgar evaluation results keeps being abnormal within the 10 minutes, the evaluation time will be extended and the Apgar evaluation for the newborn will continue.

S42, displaying a newborn evaluation interface when the duration reaches the condition for newborn scoring.

Wherein, the newborn evaluation interface comprises more than or equal to two scoring items.

when monitoring the target newborn, the monitoring equipment displays the newborn monitoring interface in a normal monitoring mode, wherein real-time values of the physiological parameters of the target newborn and the target physiological parameters as well as the corresponding alarm threshold are displayed on the interface. when the duration reaches the condition for newborn scoring, the newborn evaluation interface is displayed on the monitoring interface. The newborn evaluation interface may be displayed on the same screen as the newborn monitoring interface without adversely affecting each other; it may also be that the newborn evaluation interface covers all or part of the newborn monitoring interface, and the two interfaces may be switched to each other.

After the newborn scoring, the medical staff may manually switch to the newborn monitoring interface, or the monitoring equipment may automatically switch, or maintain the current status without switching until the Apgar evaluation is finished.

The newborn evaluation interface comprises at least two scoring items, such as skin color, pulse/heart rate, response to stimulus, and so on. Of course, these are only some examples and do not limit the protection scope of the present disclosure, and it may be set according to actual needs. Optionally, the newborn evaluation interface also displays scoring standards of each scoring item.

Figure 12:
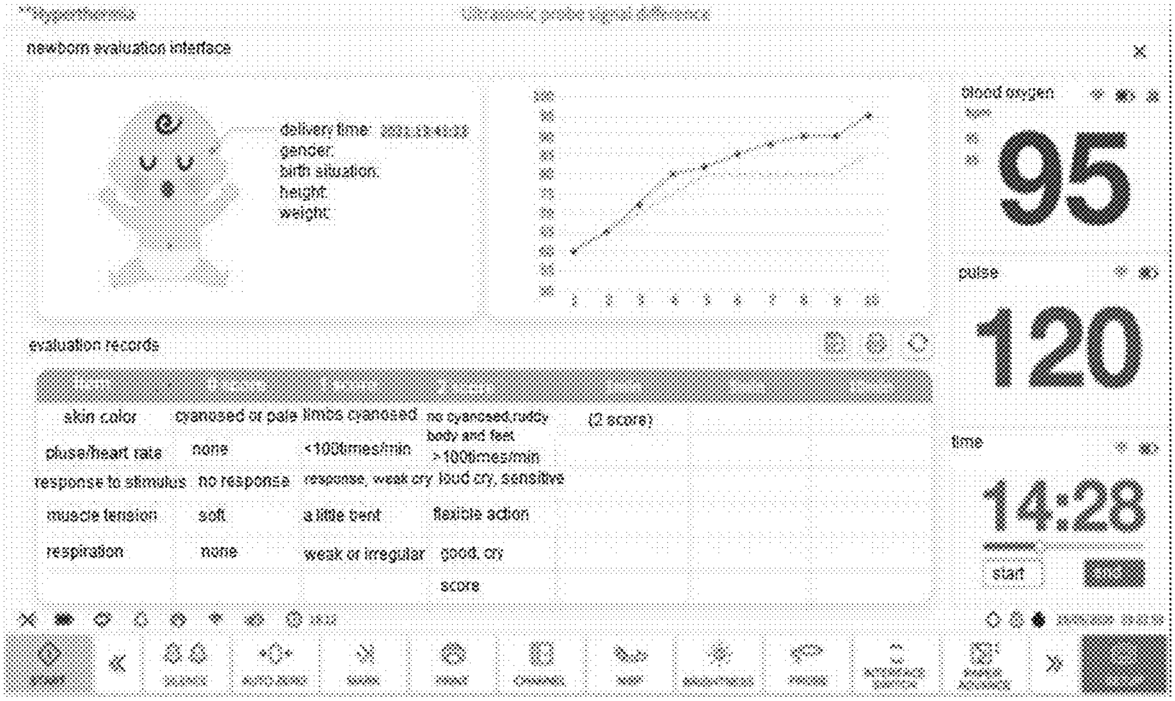
FIG. 12 is a schematic diagram of a newborn evaluation interface according to an embodiment of the present disclosure.

In some optional implementations of this embodiment, the newborn evaluation interface comprises a newborn scoring table, and the newborn scoring table comprises at least two scoring items. As shown in FIG. 12, in the newborn evaluation interface, the newborn score table is used to represent the score items of the target newborn, and the newborn score table also comprises the scoring standards of each scoring item.

S43, obtaining a scoring result for each scoring item, and determining a score value of the target newborn for each time of scoring.

As mentioned above, the scoring items include physiological parameters and body characterization items. For the scoring result corresponding to physiological parameters, the real-time value of each physiological parameter may be acquired first, and the scoring result may be determined by comparing it with the scoring standard thereof; the scoring result corresponding to the physical representation items may be manually input by medical staff.

After the scoring results of each scoring item are obtained for each time of scoring, the monitoring equipment calculates a scoring value of the target newborn at this time of scoring, for example, the scoring results of each scoring item are summed or weighted, and so on.

As shown in FIG. 12, the monitoring equipment displays the newborn monitoring interface, and displays the newborn evaluation interface every 5 minutes to determine the score value for each time of evaluation. Specifically, the newborn evaluation interface pops up at 1 minute, 5 minutes and 10 minutes, and the score values for each time of evaluation are calculated respectively. Specifically, the time-after-delivery is recorded, and a timer is displayed in a corresponding area of the newborn monitoring interface. when it reaches the first time point of 1 minute, the monitoring equipment sends out an audio prompt, and a newborn evaluation interface pops up, so that the information at this time point can be entered. when the second time point is reached, an audio prompt will be sent out, and a newborn scoring interface will pop up, so the information at this time point can be entered. when the third time point is reached, an audio prompt will be sent out, and a newborn scoring box will pop up, so the information at this time point can be entered.

The monitoring equipment may compare the score value for each time of evaluation with preset conditions to determine whether the target newborn is abnormal. when an abnormality is determined on the basis of the scoring value for each time of scoring, step S433 is executed; otherwise, other operations are performed. Wherein, other operations may be to return to the newborn monitoring interface, or to stay on the newborn evaluation interface to wait for the next time of scoring.

Specifically, step S43 mentioned above comprises:

S431, obtaining the scoring result for each scoring item at each time of scoring, and correspondingly displaying the scoring result in the newborn scoring table.

The monitoring equipment obtains the scoring result for each scoring item at each time of scoring, and displays the scoring results for each time of scoring at the corresponding evaluation time point, which is displayed in the newborn scoring table. As shown in FIG. 12, there are displayed scores corresponding to time points of 1 minute, 5 minutes and 10 minutes respectively. when the monitoring equipment determines the score value for each time of scoring, it displays the score value in a corresponding area of the newborn scoring table.

S432, determining the score value of the target newborn for each time of scoring on the basis of each score result in the newborn scoring table.

when the score value for each time of scoring keeps being less than a preset threshold for a first preset time period, step S433 is executed; otherwise, the newborn monitoring interface is displayed. Wherein, the first preset time period and the preset threshold may be set according to the actual needs, and there is no limitation on them herein.

S433, determining there is an abnormality for the target newborn and adding a scoring column into the newborn scoring table to continue scoring the target newborn.

For example, for a newborn whose Apgar score is less than 7 at 5 minutes after birth, the newborn should be re-evaluated every 5 minutes until 20 minutes after birth or a preset time. As shown in FIG. 12, the newborn scoring table is also updated to an expanded Apgar scoring table. In addition to the above-mentioned items of muscle tension, pulse, respiration, skin color and response to stimulus, the respective scoring items also comprise options for resuscitation events and medications, including events such as intubation, oxygen supply, positive pressure ventilation, chest compression and medication administration, etc; as well as medications such as epinephrine, normal saline and other medication names, concentration, mode (intravenous administration, rapid administration) and time for administration of medication.

S44, displaying an abnormality alert on the newborn evaluation interface.

when the monitoring equipment determines that the target newborn is abnormal, it displays an abnormality alert on the newborn evaluation interface, for example, displaying selectable monitoring events, matters needing attention, etc.

Figure 13:
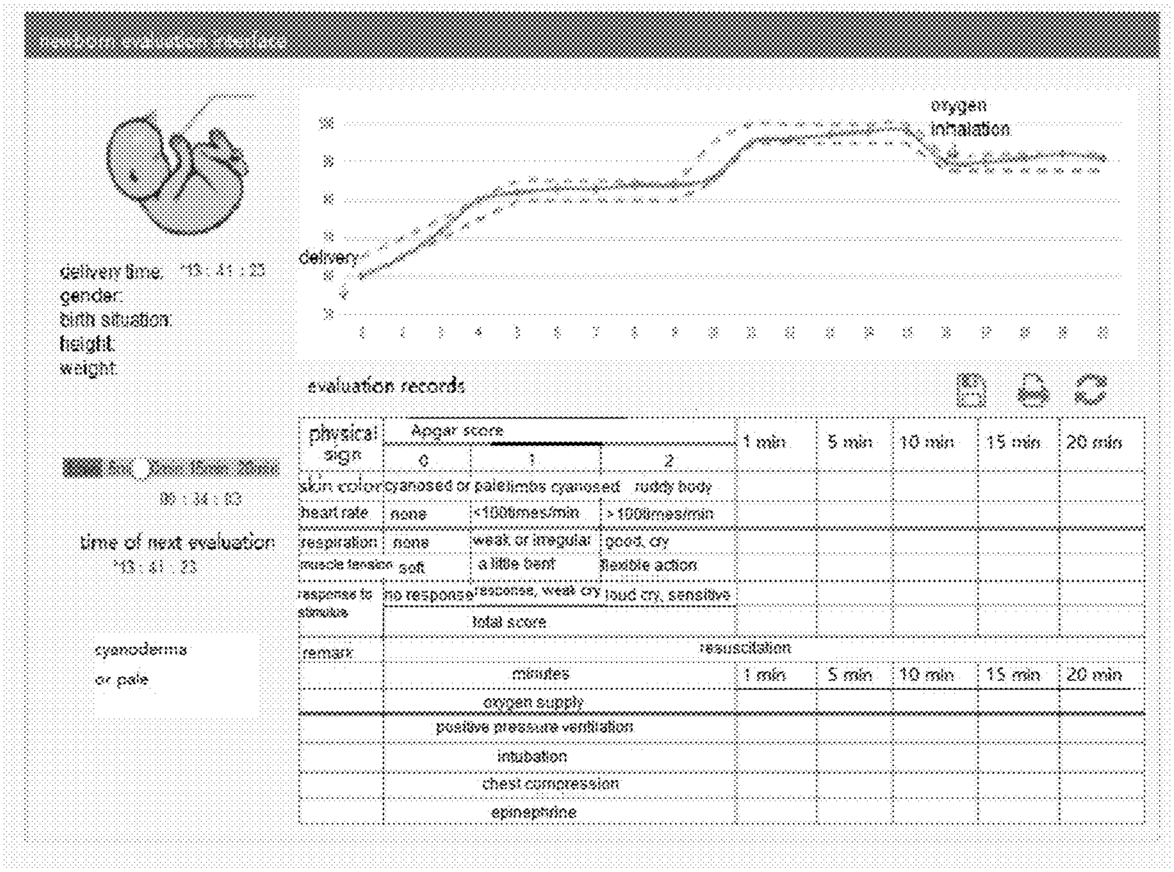
FIG. 13 is a schematic diagram of a newborn evaluation interface according to another embodiment of the present disclosure.

In some optional implementations of this embodiment, the abnormality alert comprises selectable monitoring events and medications, and the newborn evaluation interface comprises an abnormality handling table. On the basis of this, the above step S44 may comprise:

S441, displaying information of selectable monitoring events and selectable medications in the abnormality handling table for selecting a monitoring event and a target medication corresponding to the target newborn.

when it is determined that there is an abnormality, the newborn scoring table in the newborn evaluation interface is expanded to the newborn score table plus the abnormality handling table. As shown in FIG. 13, the information of selectable monitoring events and selectable medications is displayed in the abnormality handling table, and the medical staff selects the corresponding information in the abnormality handling table. Accordingly, the monitoring equipment may obtain a monitoring event and a target medication corresponding to the target newborn when the selection operation of the medical staff.

Accordingly, when the occurrence of a monitoring event is detected for the target newborn, the monitoring equipment needs to adjust the alarm threshold of the target physiological parameters on the basis of the monitoring event. Please refer to the corresponding description of the embodiments shown in FIG. 6 or FIG. 8 above for the specific adjustment mode thereof, which will not be repeated herein.

S442, displaying the selected monitoring event and the selected target medication in the abnormality handling table.

The monitoring equipment displays the monitoring event and the target medications selected by the medical staff at each time of scoring in the abnormality handling table.

In some optional implementations of this embodiment, the newborn evaluation interface comprises a monitoring parameter display area, and the method comprises displaying real-time values of physiological parameter corresponding thereto and an adjusted alarm threshold corresponding thereto in the monitoring parameter display area.

Specifically, as shown in FIG. 13, the corresponding physiological parameters of the target newborn and the adjusted alarm threshold on the basis of the monitoring event are displayed on the newborn evaluation interface at the same time. That is, the physiological parameters are monitored at the same time when the target newborn is treated with the monitoring event.

The real-time values of physiological parameters and the corresponding adjusted alarm threshold are displayed at the same time when handling the abnormality, so that, at the same time of handling the abnormality, the monitoring parameters of the target newborn can be obtained and observed in time.

The monitoring method provided by this embodiment automatically displays the newborn evaluation interface when the condition for newborn scoring is reached, calculates the scoring result of each scoring item to obtain a score value for each time of scoring, and displays an abnormality alert on the newborn evaluation interface when it is determined there is an abnormality, which is convenient for medical staff to know the abnormal situation in time, so as to make corresponding nursing operations and ensure the reliability of newborn monitoring. Wherein, when it is determined that the score value keeps being less than the preset threshold for the first preset time period, a score column is added to continue scoring the target newborn, so as to prevent false alarm of an abnormal score value caused by other factors and ensure the accuracy of monitoring; when the score value is greater than or equal to the preset threshold value during the first preset time period, it means that the target newborn is normal, and it is switched to the newborn monitoring interface for routine monitoring.

Figure 14:
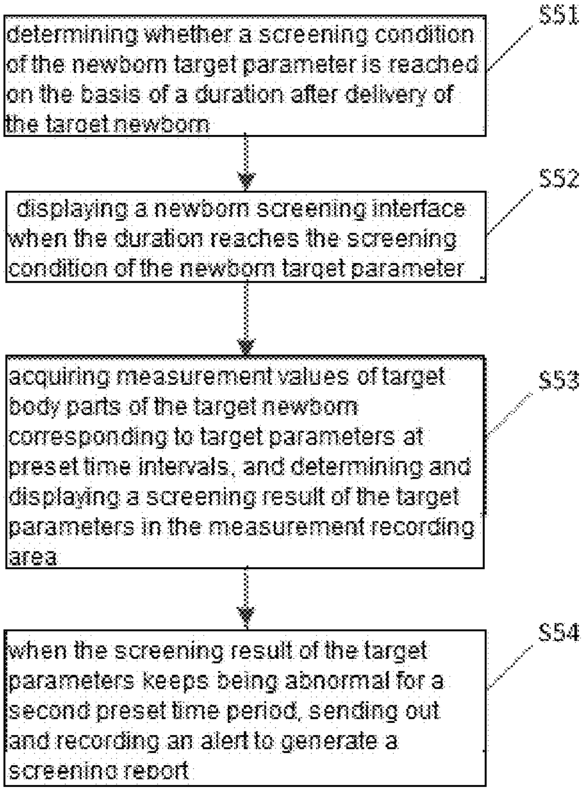
FIG. 14 is a flowchart of a monitoring method according to an embodiment of the present disclosure.

In this embodiment, a monitoring method is provided, which may be applied to the above monitoring equipment. In addition to routine monitoring for a newborn, different monitoring objects may also be evaluated according to a duration after delivery. For example, in the embodiment shown in FIG. 11, the newborn is scored for a period of time starting from delivery, and the newborn is also screened for target parameters when a certain duration after delivery has elapsed, that is, the embodiment shown in FIG. 14. The monitoring method described in FIG. 14 is on the basis of the monitoring method described in FIG. 6 and FIG. 8, and may coexist with the monitoring method described in FIG. 11. For example, the target newborn is monitored differently at different stages on the basis of the duration after delivery.

FIG. 14 is a flowchart of a monitoring method according to an embodiment of the present disclosure. As shown in FIG. 14, the flowchart comprises the following steps:

S51, determining whether a screening condition of the newborn target parameter is reached on the basis of a duration after delivery of the target newborn.

The screening condition of each newborn target parameter is set according to the monitoring requirements. For example, a screening condition of target parameter A is 20 minutes after delivery; the screening condition of target parameter B is 6 hours after delivery, and so on. These are all set according to the actual needs, and there is no limitation on them herein. In this embodiment, it is described that when the duration after delivery reaches the screening condition of a particular newborn target parameter, the screening process of this particular target parameter is carried out on the target newborn.

S52, displaying a newborn screening interface when the duration reaches the screening condition of the newborn target parameter.

Wherein, the newborn screening interface comprises a measurement recording area.

The newborn screening interface is displayed according to a relationship between the duration after delivery and the screening condition. when the screening condition is reached, the newborn screening interface will pop up on the interface of the monitoring equipment. when a measuring operation is finished, it returns to the newborn monitoring interface for display.

Figure 15:
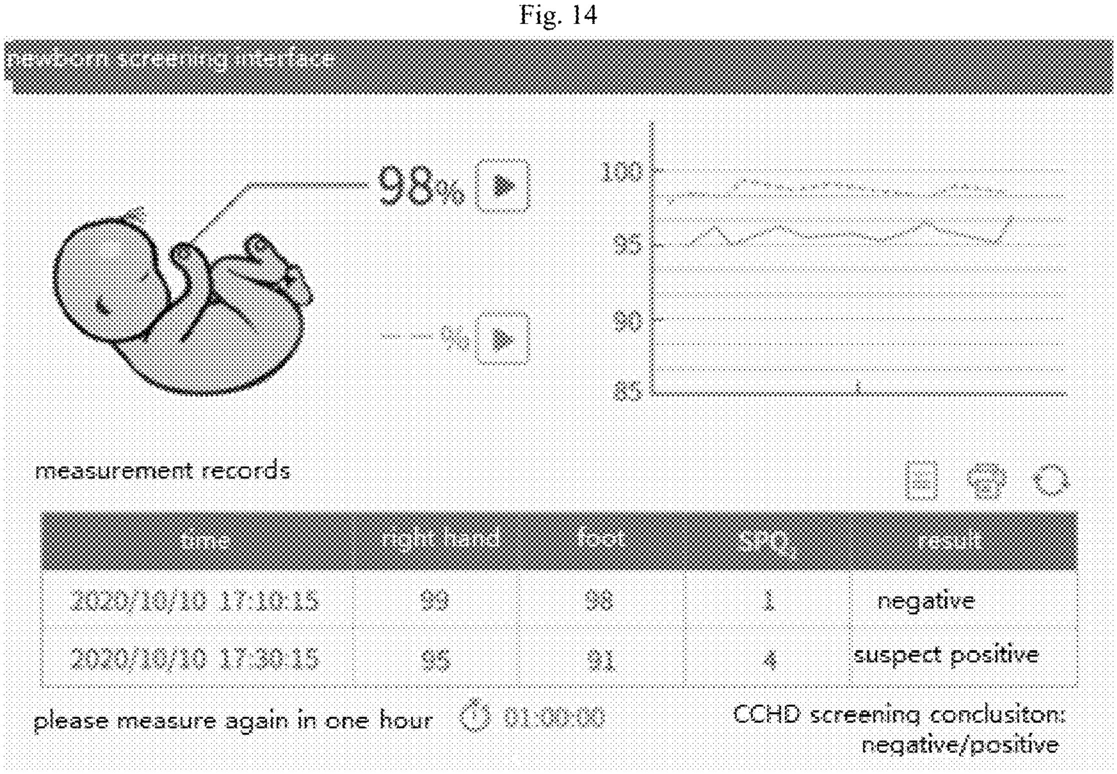
FIG. 15 is a schematic diagram of a newborn screening interface according to an embodiment of the present disclosure.

As shown in FIG. 15, the time of each screening and the corresponding measurement results are displayed on the newborn screening interface.

S53, acquiring measurement values of target body parts of the target newborn corresponding to target parameters at preset time intervals, and determining and displaying a screening result of the target parameters in the measurement recording area.

The monitoring equipment displays the newborn screening interface at preset time intervals, and the monitoring equipment acquires the measurement values of the target body parts of the target newborn corresponding to the target parameters and displays them in corresponding areas on the newborn screening interface. At each time of screening, a screening result of the target parameters is displayed in a corresponding area.

S54: when the screening result of the target parameters keeps being abnormal for a second preset time period, sending out and recording an alert to generate a screening report.

If the monitoring equipment determines that the screening result of the target parameters keeps being abnormal for a second preset time period, it would send out an alert and record it, and finally generate a screening report.

As shown in FIG. 15, within 6-72 hours after the delivery of a newborn, the CHDD (congenital heart disease) may be evaluated through the newborn screening interface. when an oxygen saturation of the newborn's right hand or either foot is ≤90%, or an oxygen saturation difference between the right hand and either foot is ≥3%, and this phenomenon is repeated for 2-4 hours, it will be alerted and recorded, and a screening report will be generated.

The monitoring method provided by this embodiment displays the newborn screening interface when a screening condition of the target parameters are reached, obtains the measurement values of the target body parts and displays them, so as to display the screening results in the recording area of the measurement parameters, and the whole process is automatically realized, thus improving the monitoring efficiency.

In this embodiment, a monitoring apparatus is also provided, which is configured to implement the above-mentioned embodiments and implementing ways thereof, and the description thereof is not repeated herein. As used below, the term "module" may be a combination of software and/or hardware that implements a predetermined function. Although the apparatus described in the following embodiment is preferably implemented by software, the implementation by hardware, or a combination of software and hardware, is also possible and contemplated.

Figure 16:
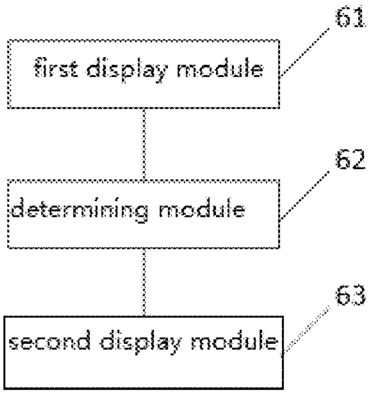
FIG. 16 is a structural block diagram of a monitoring apparatus according to an embodiment of the present disclosure.

This embodiment provides a monitoring apparatus, as shown in FIG. 16, comprising:

a first display module 61, configured to display maternal physiological parameters and fetal physiological parameters respectively in a mother monitoring area and a fetus monitoring area of a monitoring interface;

a determining module 62, configured to determine current stage-of-labor progress on the basis of types of acquired monitoring parameters;

a second display module 63, configured to determine a monitoring object on the basis of the current stage-of-labor progress, and display corresponding monitoring parameters in areas corresponding to each monitoring object on the monitoring interface, wherein the monitoring interface comprises one or a plurality of the mother monitoring area, the fetus monitoring area and a newborn monitoring area.

The monitoring apparatus in this embodiment is presented in the form of functional units, wherein the units refer to ASIC circuits, processors and memories that execute one or more software or firmware, and/or other devices that can provide the above functions.

Further functional descriptions of the above-mentioned modules are the same as those of the above-mentioned corresponding embodiments, and are not repeated herein.

The embodiments of the present disclosure also provide a non-transitory computer storage medium, and the computer storage medium stores computer-executable instructions that can execute the monitoring method according to any one of the above method embodiments. The storage medium may be a magnetic disk, an optical disk, a Read-Only Memory (ROM), a Random Access Memory (RAM), a Flash Memory, a Hard Disk Drive (HDD) or a Solid-State Drive (SSD), etc. The storage medium may also comprise a combination of the above kinds of memories.

Although the embodiments of the present disclosure have been described in connection with the appended drawings, those skilled in this art may make various modifications and variations without departing from the spirit and scope of the present disclosure, and such modifications and variations are all within the scope defined by the appended claims.

The invention claimed is:

1. A monitoring equipment, comprising:

a measurement unit, configured to acquire monitoring parameters;

a control unit, connected with the measurement unit and configured to determine current stage-of-labor progress on the basis of types of the acquired monitoring parameters, so as to determine monitoring objects, wherein the monitoring objects comprises a mother and a fetus and a newborn, or comprises a mother and a fetus; and a display unit, connected with the control unit and configured to display corresponding monitoring parameters in an area corresponding to each monitoring object on a monitoring interface, wherein the monitoring interface comprises at least one of a mother monitoring area, a fetus monitoring area and a newborn monitoring area;

wherein the measurement unit comprises:

a maternal parameter measuring apparatus, configured to measure monitoring parameters of the mother that include uterine contraction pressure, uterine myoelectricity, intrauterine pressure, ECG, respiration, blood pressure, blood oxygen, pulse and body temperature;

a fetal parameter measuring apparatus, configured to measure monitoring parameters of the fetus that include fetal heart rate and fetal ECG; and a neonatal parameter measuring apparatus, configured to measure monitoring parameters of the newborn that at least include neonatal blood oxygen;

wherein the display unit is configured to display a newborn monitoring interface in response to a selection operation of selecting the newborn monitoring area, wherein the newborn monitoring interface comprises an alarm area;

the control unit is configured to, when a monitoring event corresponding to a target newborn is received, adjusting an alarm threshold of target physiological parameters on the basis of the monitoring event; and the display unit is configured to display real-time values of the target physiological parameters and the adjusted alarm threshold in the alarm area.

2. The monitoring equipment according to claim 1, wherein the neonatal parameter measuring apparatus comprises one or a plurality of accessory interfaces, which are configured to be connected with a neonatal parameter measuring accessory.

3. The monitoring equipment according to claim 1, wherein the neonatal parameter measuring apparatus comprises one or a plurality of neonatal parameter measuring modules arranged within the monitoring equipment.

4. A monitoring system, comprising:

the monitoring equipment according to claim 1;

one or a plurality of neonatal parameter measuring equipment, connected with the monitoring equipment; and a monitoring workstation, the monitoring workstation being respectively communicationally connected with the monitoring equipment and the one or a plurality of neonatal parameter measuring equipment.

5. A monitoring method, which is applied to the monitoring equipment according to claim 1, comprising:

displaying maternal physiological parameters and fetal physiological parameters respectively in a mother monitoring area and a fetus monitoring area of a monitoring interface;

determining current stage-of-labor progress on the basis of types of acquired monitoring parameters; and determining a monitoring object on the basis of the current stage-of-labor progress, and displaying corresponding monitoring parameters in areas corresponding to each monitoring object on the monitoring interface, wherein the monitoring interface comprises at least one of the mother monitoring area, the fetus monitoring area and a newborn monitoring area;

wherein the monitoring parameters are acquired by:

using a maternal parameter measuring apparatus to measure monitoring parameters of a mother that include uterine contraction pressure, uterine myoelectricity, intrauterine pressure, ECG, respiration, blood pressure, blood oxygen, pulse and body temperature;

using a fetal parameter measuring apparatus to measure monitoring parameters of a fetus that include fetal heart rate and fetal ECG; and using a neonatal parameter measuring apparatus to measure monitoring parameters of a newborn that at least include neonatal blood oxygen;

wherein the method further comprises:

displaying a newborn monitoring interface in response to a selection operation of selecting the newborn monitoring area, wherein the newborn monitoring interface comprises an alarm area;

when a monitoring event corresponding to a target newborn is received, adjusting an alarm threshold of target physiological parameters on the basis of the monitoring event; and displaying real-time values of the target physiological parameters and the adjusted alarm threshold in the alarm area.

6. The method according to claim 5, wherein, when the current stage-of-labor progress is that one or more fetuses have all been delivered:

the monitoring object comprises a mother and one or more newborns, and the step of displaying corresponding monitoring parameters in areas corresponding to each monitoring object on the monitoring interface comprises:

displaying neonatal physiological parameters in the newborn monitoring area; and displaying maternal physiological parameters in the mother monitoring area.

7. The method according to claim 5, wherein, when the current stage-of-labor progress is that fetuses have partially been delivered:

the monitoring object comprises a mother, a newborn and a fetus, and the step of displaying corresponding monitoring parameters in areas corresponding to each monitoring object on the monitoring interface comprises:

displaying neonatal physiological parameters in the newborn monitoring area;

displaying fetal physiological parameters in the fetus monitoring area; and displaying maternal physiological parameters in the mother monitoring area.

8. The method according to claim 6, when the fetuses have all been delivered, the step of displaying corresponding monitoring parameters in areas corresponding to each monitoring object on the monitoring interface comprises:

displaying the fetus monitoring area on the monitoring interface.

9. The method according to claim 5, wherein the step of adjusting an alarm threshold of target physiological parameters on the basis of the monitoring event comprises:

displaying an initial alarm threshold along with time-after-delivery of newborn in the alarm area;

when the monitoring event corresponding to the target newborn is received, on the basis of a time point and a type of the monitoring event, adjusting the initial alarm threshold corresponding to the time point and a duration after the time point.

10. The method according to claim 9, wherein:

the initial alarm threshold comprises an upper alarm limit and/or a lower alarm limit, and the step of displaying the adjusted alarm threshold in the alarm area comprises:

displaying adjusted upper alarm limit and/or adjusted lower alarm limit in the alarm area, and marking the type of the monitoring event in a zone of the alarm area corresponding to the time point.

11. The method according to claim 5, wherein the target physiological parameters comprise blood oxygen, and the step of displaying real-time values of the target physiological parameters and the adjusted alarm threshold in the alarm area comprises:

displaying a curve of the blood oxygen and a curve of the alarm threshold in the alarm area.

12. The method according to claim 5, wherein the method comprises:

counting a duration after delivery of the target newborn, and determining whether a condition for newborn scoring is reached on the basis of the duration;

displaying a newborn evaluation interface when the duration reaches the condition for newborn scoring, wherein the newborn evaluation interface comprises more than or equal to two scoring items;

obtaining a scoring result for each scoring item, and determining a score value of the target newborn for each time of scoring; and when an abnormality is determined on the basis of the score value for each time of scoring, displaying an abnormality alert on the newborn evaluation interface.

13. The method according to claim 12, wherein:

the newborn evaluation interface comprises a newborn scoring table, the newborn scoring table comprises the more than or equal to two scoring items, and the step of obtaining a scoring result for each scoring item and determining a score value of the target newborn for each time of scoring comprises:

obtaining the scoring result for each scoring item at each time of scoring, and correspondingly displaying the scoring result in the newborn scoring table;

determining the score value of the target newborn for each time of scoring on the basis of each score result in the newborn scoring table; and when the score value for each time of scoring keeps being less than a preset threshold for a first preset time period, determining there is an abnormality and adding a scoring column into the newborn scoring table to continue scoring the target newborn.

14. The method according to claim 13, wherein the step of obtaining a scoring result for each scoring item and determining a score value of the target newborn for each time of scoring comprises:

when the score value for each time of scoring is greater than or equal to the preset threshold during the first preset time period, displaying the newborn monitoring interface.

15. The method according to claim 12, wherein:

the abnormality alert comprises selectable monitoring events and selectable medications, the newborn evaluation interface comprises an abnormality handling table, and the step of displaying the abnormality alert on the newborn evaluation interface comprises:

displaying information of selectable monitoring events and selectable medications in the abnormality handling table for selecting a monitoring event and a target medication corresponding to the target newborn;

displaying the selected monitoring event and the selected target medication in the abnormality handling table.

16. The method according to claim 12, wherein:

the newborn evaluation interface comprises a monitoring parameter display area, and the method further comprises:

displaying real-time values of physiological parameters corresponding thereto and an adjusted alarm threshold corresponding thereto in the monitoring parameter display area.

17. The method according to claim 5, wherein the method comprises:

determining whether a screening condition of the newborn target parameter is reached on the basis of a duration after delivery of the target newborn;

displaying a newborn screening interface when the duration reaches the screening condition of the newborn target parameter, wherein the newborn screening interface comprises a measurement recording area; and acquiring measurement values of target body parts of the target newborn corresponding to target parameters at preset time intervals, and determining and displaying a screening result of the target parameters in the measurement recording area.

18. The method according to claim 17, wherein the method comprises:

when the screening result of the target parameters keeps being abnormal for a second preset time period, sending out and recording an alert to generate a screening report.

* * * * *